United States Patent
Hagiya

(10) Patent No.: US 8,399,710 B2
(45) Date of Patent: Mar. 19, 2013

(54) ALKALI METAL FLUORIDE DISPERSION AND PROCESS FOR PRODUCING FLUORINE-CONTAINING ORGANIC COMPOUND USING THE SAME

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 385 days.

(21) Appl. No.: 12/675,042

(22) PCT Filed: Aug. 27, 2008

(86) PCT No.: PCT/JP2008/065796
§ 371 (c)(1),
(2), (4) Date: Feb. 24, 2010

(87) PCT Pub. No.: WO2009/028719
PCT Pub. Date: Mar. 5, 2009

(65) Prior Publication Data
US 2011/0112321 A1    May 12, 2011

(30) Foreign Application Priority Data
Aug. 29, 2007 (JP) ................................. 2007-222201

(51) Int. Cl.
*C07C 45/90* (2006.01)

(52) U.S. Cl. ........ 568/433; 568/437; 568/814; 568/937; 568/938; 560/83; 570/123

(58) Field of Classification Search .................. None
See application file for complete search history.

(56) References Cited

U.S. PATENT DOCUMENTS

| | | | |
|---|---|---|---|
| 4,642,398 A * | 2/1987 | Cantrell | 568/937 |
| 4,849,552 A | 7/1989 | Cantrell | |
| 6,127,581 A | 10/2000 | Wiedemann et al. | |
| 2009/0099387 A1 | 4/2009 | Hagiya et al. | |

FOREIGN PATENT DOCUMENTS

| | | |
|---|---|---|
| JP | 58 65226 | 4/1983 |
| JP | 58-65226 | 4/1983 |
| JP | 58-157727 | 9/1983 |
| JP | 58-199715 | 11/1983 |
| JP | 61-50945 | 3/1986 |
| JP | 63-10737 | 1/1988 |
| JP | 63-89417 | 4/1988 |
| JP | 63 502181 | 8/1988 |
| JP | 2 11571 | 3/1990 |
| JP | 2-111624 | 4/1990 |
| JP | 2 111624 | 4/1990 |
| JP | 4-6104 | 1/1992 |
| JP | 2000 86553 | 3/2000 |
| WO | WO 87/04151 | 7/1987 |
| WO | 2007 126142 | 11/2007 |
| WO | WO 2007/126142 A1 | 11/2007 |

OTHER PUBLICATIONS

U.S. Appl. No. 13/341,069, filed Dec. 30, 2011, Hagiya, et al.
Timothy P. Smyth, et al., "Inexpensive, Active KF for Nucleophilic Aromatic Displacement Reactions.", Tetrahedron, vol. 51, No. 22, 1995, pp. 6363-6376.

* cited by examiner

Primary Examiner — Sudhakar Katakam
(74) Attorney, Agent, or Firm — Oblon, Spivak, McClelland, Maier & Neustadt, L.L.P.

(57) ABSTRACT

An alkali metal fluoride dispersion of an alkali metal fluoride and an aprotic organic solvent is obtainable by (A) separating a liquid phase from an alkali metal fluoride dispersion comprising an alcohol solvent and an alkali metal fluoride, and mixing the separated liquid phase with an aprotic organic solvent having a boiling point of 85° C. or higher at normal pressure; (B) obtaining a mixture containing the alkali metal fluoride by (b1) concentrating the mixture containing the alkali metal fluoride to obtain a concentrated fraction and a concentrated residue; (b2) mixing a residue of the alkali metal fluoride dispersion with the concentrated fraction obtained in (b1); and (b3) separating a liquid phase from the mixture containing an alkali metal fluoride obtained in (b2) and mixing the separated liquid phase with the concentrated residue; and (C) removing the alcohol solvent from the mixture containing the alkali metal fluoride.

8 Claims, No Drawings

ALKALI METAL FLUORIDE DISPERSION AND PROCESS FOR PRODUCING FLUORINE-CONTAINING ORGANIC COMPOUND USING THE SAME

TECHNICAL FIELD

The present invention relates to an alkali metal fluoride dispersion and a process for producing a fluorine-containing organic compound using the same.

BACKGROUND ART

Alkali metal fluorides are useful as fluorinating agents for an organic compound. WO87/04151 discloses that a method for preparing a potassium fluoride dispersion by mixing 27.5 g of potassium fluoride with 50 mL of methanol to prepare a potassium fluoride solution, mixing the potassium fluoride solution with 55.2 g of sulfolane and 50 mL of toluene, and concentrating the obtained mixture to remove methanol and toluene, and a method for fluorinating an organic compound using the prepared potassium fluoride dispersion.

DISCLOSURE OF THE INVENTION

The present invention is to provide
<1> An alkali metal fluoride dispersion essentially consisting of an alkali metal fluoride and an aprotic organic solvent obtainable by conducting the following Step (A), subsequently conducting the following Step (B) at least once, and then conducting the following Step(C);

Step (A): a step of separating a liquid phase from an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride;

Step (B): a step of obtaining a mixture containing the alkali metal fluoride comprising the following Steps (b1) to (b3);

Step (b1): a step of concentrating the mixture containing the alkali metal fluoride, which is obtained in Step (A) or Step (b3), to obtain a concentrated fraction and a concentrated residue;

Step (b2): a step of mixing a residue of the alkali metal fluoride dispersion obtained by separating the liquid phase in Step (A) or a residue of the mixture obtained by separating a liquid phase in Step (b3) with the concentrated fraction obtained in Step (b1) to obtain a mixture containing an alkali metal fluoride; and Step (b3): a step of separating a liquid phase from the mixture containing an alkali metal fluoride, which is obtained in Step (b2), and mixing the separated liquid phase with the concentrated residue obtained in Step (b1) to obtain a mixture containing an alkali metal fluoride; and Step (C): a step of removing the alcohol solvent from the mixture containing the alkali metal fluoride, which is obtained in Step (B), to obtain the alkali metal fluoride dispersion essentially consisting of the alkali metal fluoride and the aprotic organic solvent;

<2> A process for producing an alkali metal fluoride dispersion essentially consisting of an alkali metal fluoride and an aprotic organic solvent obtainable by conducting the following Step (A), subsequently conducting the following Step (B) at least once, and then conducting the following Step(C);

Step (A): a step of separating a liquid phase from an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride;

Step (B): a step of obtaining a mixture containing the alkali metal fluoride comprising the following Steps (b1) to (b3);

Step (b1): a step of concentrating the mixture containing the alkali metal fluoride, which is obtained in Step (A) or Step (b3), to obtain a concentrated fraction and a concentrated residue;

Step (b2): a step of mixing a residue of the alkali metal fluoride dispersion obtained by separating the liquid phase in Step (A) or a residue of the mixture obtained by separating a liquid phase in Step (b3) with the concentrated fraction obtained in Step (b1) to obtain a mixture containing an alkali metal fluoride; and Step (b3): a step of separating a liquid phase from the mixture containing an alkali metal fluoride, which is obtained in Step (b2), and mixing the separated liquid phase with the concentrated residue obtained in Step (b1) to obtain a mixture containing an alkali metal fluoride; and Step (C): a step of removing the alcohol solvent from the mixture containing the alkali metal fluoride, which is obtained in Step (B), to obtain the alkali metal fluoride dispersion essentially consisting of the alkali metal fluoride and the aprotic organic solvent;

<3> The process according to <2>, wherein the used amount of the alcohol solvent in Step (A) is less than 5 parts by weight per 1 part by weight of the alkali metal fluoride;

<4> The process according to <2> or <3>, wherein the concentrated fraction obtained in Step (b1) is a fraction essentially consisting of the alcohol solvent;

<5> The process according to any one of <2> to <4>, wherein Step (A) to Step (B) is continuously conducted;

<6> The process according to any one of <2> to <5>, wherein the alkali metal fluoride is potassium fluoride or cesium fluoride;

<7> The process according to any one of <2> to <6>, wherein the alcohol solvent is methanol or ethanol;

<8> The process according to any one of <2> to <5>, wherein the alkali metal fluoride is potassium fluoride and the alcohol solvent is methanol;

<9> The process according to any one of <2> to <8>, wherein the aprotic organic solvent is an aprotic polar solvent;

<10> The process according to <9>, wherein the aprotic polar solvent is a sulfone solvent or a sulfoxide solvent;

<11> A process for producing a fluorine-containing organic compound comprising contacting an organic compound having at least one group capable of being substituted nucleophilically with a fluorine atom with the alkali metal fluoride dispersion according to <1>;

<12> The process according to <11>, wherein the organic compound is an aliphatic hydrocarbon compound which may be substituted with a group not being involved in a fluorination reaction;

<13> The process according to <11>, wherein the organic compound is an aromatic hydrocarbon compound which may be substituted with a group not being involved in a fluorination reaction;

<14> The process according to <11>, wherein the organic compound is a heteroaromatic compound which may be substituted with a group not being involved in a fluorination reaction;

<15> The process according to any one of <11> to <14>, wherein the group capable of being substituted nucleophilically with a fluorine atom is a chlorine atom, a bromine atom, an iodine atom, a nitro group, a sulfo group, an optionally substituted alkylsulfonyloxy group, an optionally substituted arylsulfonyloxy group or an optionally substituted acyloxy group;

<16> The process according to <11>, wherein the organic compound having at least one group capable of being substituted nucleophilically with a fluorine atom is tetrachloroterephthalic dichloride;

<17> A process for producing a tetrafluoroterephthalic acid diester comprising reacting tetrafluoroterephthalic difluoride obtained according to the process described in <16> with an alcohol;

<18> Use of the alkali metal fluoride dispersion according to <1> for fluorinating an organic compound having at least one group capable of being substituted nucleophilically with a fluorine atom;

<19> Use of the alkali metal fluoride dispersion obtained according to any one of <2> to <10> for fluorinating an organic compound having at least one group capable of being substituted nucleophilically with a fluorine atom;

<20> A method for fluorinating an organic compound comprising contacting an organic compound having at least one group capable of being substituted nucleophilically with a fluorine atom with the alkali metal fluoride dispersion according to <1>;

<21> A method for fluorinating an organic compound comprising contacting an organic compound having at least one group capable of being substituted nucleophilically with a fluorine atom with the alkali metal fluoride dispersion obtained according to any one of <2> to <10>;

<22> A composition for fluorination essentially consisting of an alkali metal fluoride and an aprotic organic solvent obtainable by conducting the following Step (A), subsequently conducting the following Step (B) at least once, and then conducting the following Step (C);

Step (A): a step of separating a liquid phase from an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride;

Step (B): a step of obtaining a mixture containing the alkali metal fluoride comprising the following Steps (b1) to (b3);

Step (b1): a step of concentrating the mixture containing the alkali metal fluoride, which is obtained in Step (A) or Step (b3), to obtain a concentrated fraction and a concentrated residue;

Step (b2): a step of mixing a residue of the alkali metal fluoride dispersion obtained by separating the liquid phase in Step (A) or a residue of the mixture obtained by separating a liquid phase in Step (b3) with the concentrated fraction obtained in Step (b1) to obtain a mixture containing an alkali metal fluoride; and Step (b3): a step of separating a liquid phase from the mixture containing an alkali metal fluoride, which is obtained in Step (b2), and mixing the separated liquid phase with the concentrated residue obtained in Step (b1) to obtain a mixture containing an alkali metal fluoride; and Step (C): a step of removing the alcohol solvent from the mixture containing the alkali metal fluoride, which is obtained in Step (B), to obtain the alkali metal fluoride dispersion essentially consisting of the alkali metal fluoride and the aprotic organic solvent.

BEST MODE FOR CARRYING OUT THE PRESENT INVENTION

First, the alkali metal fluoride dispersion essentially consisting of an alkali metal fluoride and an aprotic organic solvent of the present invention (hereinafter, sometimes simply referred to as the present dispersion) and the process for producing thereof are illustrated.

The present dispersion consists essentially of an alkali metal fluoride and an aprotic organic solvent, and is a mixture wherein a fine powder of the alkali metal fluoride disperses in the aprotic organic solvent. The content of the alkali metal fluoride in the present dispersion is usually in a range of 5 to 70% by weight.

The present dispersion can be produced by conducting the following Step (A), subsequently conducting the following Step (B) at least once, and then conducting the following Step(C);

Step (A): a step of separating a liquid phase from an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride;

Step (B): a step of obtaining a mixture containing the alkali metal fluoride comprising the following Steps (b1) to (b3);

Step (b1): a step of concentrating the mixture containing the alkali metal fluoride, which is obtained in Step (A) or Step (b3), to obtain a concentrated fraction and a concentrated residue;

Step (b2): mixing a residue of the alkali metal fluoride dispersion obtained by separating the liquid phase in Step (A) or a residue of the mixture obtained by separating a liquid phase in Step (b3) with the concentrated fraction obtained in Step (b1) to obtain a mixture containing an alkali metal fluoride; and Step (b3): a step of separating a liquid phase from the mixture containing an alkali metal fluoride, which is obtained in Step (b2), and mixing the separated liquid phase with the concentrated residue obtained in Step (b1) to obtain a mixture containing an alkali metal fluoride; and Step (C): a step of removing the alcohol solvent from the mixture containing the alkali metal fluoride, which is obtained in Step (B), to obtain the alkali metal fluoride dispersion essentially consisting of the alkali metal fluoride and the aprotic organic solvent.

First, Step (A) is illustrated.

Step (A) is a step of separating a liquid phase from an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride.

Examples of the alkali metal fluoride include sodium fluoride, potassium fluoride and cesium fluoride. Potassium fluoride and cesium fluoride are preferable, and potassium fluoride is more preferable. A commercially available alkali metal fluoride may be used and an alkali metal fluoride obtained by reacting an alkali metal hydroxide with hydrogen fluoride may be used. Its hydrate may be used and its anhydrate may be used. Additionally, a hydrous one may be used.

At least one alcohol solvent selected from the group consisting of methanol, ethanol and isopropanol (hereinafter, sometimes simply referred to as the alcohol solvent), and methanol or ethanol is preferable. When potassium fluoride is used, methanol is more preferable from the viewpoint of a solubility of potassium fluoride. When cesium fluoride is used, methanol is more preferable from the viewpoint of a fluorination ability of the present dispersion obtained.

As the alcohol solvent, a commercially available one is usually used. An anhydrate alcohol solvent may be used and an alcohol solvent containing water up to about 5% by weight may be used.

The used amount of the alcohol solvent may be an amount of which the alkali metal fluoride is not completely dissolved in, and is usually less than 5 parts by weight per 1 part by weight of the alkali metal fluoride and preferably 0.1 to 4.9 parts by weight.

"Alkali metal fluoride dispersion comprising the alkali metal fluoride and the alcohol solvent" means a mixture of a liquid phase containing the alkali metal fluoride and the alcohol solvent, and a solid phase consisting of the alkali metal fluoride. The alkali metal fluoride dispersion may contain the other component or components, and examples of the other component include water and an aprotic organic solvent.

Examples of the method of separating a liquid phase from the alkali metal fluoride dispersion include a method of conducting a solid-liquid separation operation such as filtration and decantation on the alkali metal fluoride dispersion to separate a part or all of the liquid phase, and a method of adding the alcohol solvent to the alkali metal fluoride dispersion in a container such as an extraction tube to make the liquid phase overflow.

The residue of the alkali metal fluoride dispersion obtained by separating the liquid phase is usually used as it is in Step (b2) of Step (B) described below.

The separated liquid phase is mixed with an aprotic organic solvent having a boiling point of 85° C. or higher at normal pressure. By using such aprotic organic solvent, the present dispersion containing no alcohol solvent can be produced. While an aprotic nonpolar organic solvent may be used as the aprotic organic solvent, an aprotic polar solvent is preferably used from the viewpoint of being able to use the obtained present dispersion as it is for the fluorination reaction described below.

The aprotic organic solvent may be used alone and two or more thereof may be mixed to use.

Examples of the aprotic polar solvent include ether solvents such as dibutyl ether, dioxane, diethylene glycol dimethyl ether and triethylene glycol dimethyl ether; sulfone solvents such as sulfolane, dimethyl sulfone and methyl ethyl sulfone; sulfoxide solvents such as dimethylsulfoxide, diethylsulfoxide and tetramethylenesulfoxide; alkylamide solvents such as N,N-dimethylformamide, N,N-dimethylacetamide and N-methyl-2-pyrrolidone; and nitrile solvents such as propionitrile, butyronitrile and adiponitrile. The sulfone solvent, the sulfoxide solvent or the alkylamide solvent is preferable, and the sulfone solvent and the sulfoxide solvent are more preferable.

Examples of the aprotic nonpolar solvent include C7-C10 aliphatic hydrocarbon solvents such as heptane, octane, nonane and decane; and aromatic hydrocarbon solvents such as toluene and xylene.

The used amount of the aprotic organic solvent maybe usually 1 part by weight or more per 1 part by weight of the alkali metal fluoride. While there is no upper limit, the volume efficiency goes down when the amount thereof is too much, and therefore, practical amount thereof is 20 parts by weight or less.

While the mixing order of the liquid phase and the aprotic organic solvent is not limited, it is usually conducted by adding the liquid phase to the aprotic organic solvent. The liquid phase may be added at once, separately or continuously.

Next, Step (B) is illustrated. Step (B) is a step of obtaining a mixture containing the alkali metal fluoride comprising the following Steps (b1) to (b3), and it is carried out at least once.

Step (b1): a step of concentrating the mixture containing the alkali metal fluoride, which is obtained in Step (A) or Step (b3), to obtain a concentrated fraction and a concentrated residue;

Step (b2): a step of mixing a residue of the alkali metal fluoride dispersion obtained by separating the liquid phase in Step (A) or a residue of the mixture obtained by separating a liquid phase in Step (b3) with the concentrated fraction obtained in Step (b1) to obtain a mixture containing an alkali metal fluoride; and Step (b3): a step of separating a liquid phase from the mixture containing an alkali metal fluoride, which is obtained in Step (b2), and mixing the separated liquid phase with the concentrated residue obtained in Step (b1) to obtain a mixture containing an alkali metal fluoride.

Step (b1) is a step of concentrating the mixture containing the alkali metal fluoride to obtain a concentrated fraction and a concentrated residue, and as the mixture containing the alkali metal fluoride, the mixture containing the alkali metal fluoride, which is obtained in the above-mentioned Step (A), or the mixture containing the alkali metal fluoride, which is obtained in Step (b3) described below, is used.

The operation pressure in case where the mixture containing the alkali metal fluoride is concentrated in Step (b1) is usually 0.7 to 200 kPa and the operation temperature is usually 20 to 200° C.

The concentrated fraction which is obtained is usually a fraction essentially consisting of the alcohol solvent. A fraction containing the aprotic organic solvent and the alcohol solvent is sometimes obtained depending on the operation pressure and the operation temperature during the concentrating. When the fraction containing the aprotic organic solvent and the alcohol solvent is obtained, the fraction may be used as it is for Step (b2), and the alcohol solvent may be isolated from the fraction by conventional separating means such as separation and distillation and only the alcohol solvent may be used for Step (b2).

The concentrated residue which is obtained is usually a mixture containing the aprotic organic solvent and the alkali metal fluoride. The mixture may contain the alcohol solvent. The concentrated residue is usually used as it is for Step (b3) described below.

Step (b1) and the above-mentioned Step (A) may be conducted at the same time and may be conducted in stages. From the viewpoint of fluorination ability of the present dispersion obtained, Step (b1) and Step (A) is preferably conducted at the same time.

Examples of the method of conducting Step (b1) and Step (A) at the same time include a method of conducting the concentration with adding the liquid phase separated in Step (A) to the mixture containing the alkali metal fluoride to obtain the concentrated fraction and the concentrated residue.

Step (b2) is a step of mixing a residue of the alkali metal fluoride dispersion obtained by separating the liquid phase in Step (A) or a residue of the mixture obtained by separating a liquid phase in Step (b3) described below with the concentrated fraction obtained in the above-mentioned Step (b1) to obtain a mixture containing an alkali metal fluoride.

It is usually conducted by adding the concentrated fraction obtained in the above-mentioned Step (b1) to the residue of the alkali metal fluoride dispersion obtained by separating the liquid phase in Step (A) or the residue of the mixture obtained by separating a liquid phase in Step (b3) described below. The concentrated fraction may be added at once, separately or continuously.

The mixture containing an alkali metal fluoride, which is obtained in Step (b2), contains an liquid phase containing the alkali metal fluoride and the alcohol solvent, and may be a mixture of the liquid phase and a solid phase consisting of the alkali metal fluoride. The liquid phase may contain the aprotic organic solvent.

Step (b3) is a step of separating a liquid phase from the mixture containing an alkali metal fluoride, which is obtained in the above-mentioned Step (b2), and mixing the separated liquid phase with the concentrated residue obtained in the above-mentioned Step (b1) to obtain a mixture containing an alkali metal fluoride.

When the mixture containing an alkali metal fluoride, which is obtained in the above-mentioned Step (b2), contains no solid phase, the all amount of the mixture may be used for Step (b3) as the liquid phase, and a part thereof may be separated to use for Step (b3).

When the mixture containing an alkali metal fluoride, which is obtained in the above-mentioned Step (b2), contains a solid phase, the liquid phase may be separated by a method such as a method of conducting a solid-liquid separation operation such as filtration and decantation on the mixture to separate a part or all of the liquid phase, or a method of adding the alcohol solvent to the mixture in a container such as an extraction tube to make the liquid phase overflow.

The residue of the mixture obtained by separating the liquid phase is usually used as it is for the above-mentioned Step (b2).

While the mixing order of the separated liquid phase and the concentrated residue obtained in the above-mentioned Step (b1) is not limited, it is usually carried out by adding the liquid phase to the concentrated residue. The liquid phase may be added at once, separately or continuously.

The mixture containing an alkali metal fluoride thus obtained is used for Step (C), and when the mixture contains a solid phase, it is preferred that the mixture is used in the above-mentioned Step (b1), Step (B) is conducted twice or more, and a mixture containing an alkali metal fluoride and no solid phase is obtained in Step (b3).

When Step (B) is conducted twice or more, Step (b1) and Step (b3) may be carried out at the same time. Step (b1) and Step (b3) is preferably carried out at the same time from the viewpoint of the fluorination ability of the present dispersion obtained.

Examples of the method of conducting Step (b1) and Step (b3) at the same time include a method of adjusting the concentrated residue obtained in Step (b1) at a temperature higher than a boiling point of the alcohol solvent at the operation pressure and concentrating it with adding the liquid phase separated in Step (b2) thereto.

The present dispersion can be produced with an easy operation by continuously conducting the above-mentioned Step (A) to Step (B). Alternatively, Step (A) to Step (B) is preferably carried out continuously from the viewpoint of the fluorination ability of the present dispersion obtained.

Specific examples of the method of continuously conducting Step (A) to Step (B) include a method comprising adding the alcohol solvent and the aprotic organic solvent to a reaction container equipped with a reflux condenser and an extraction tube, charging the alkali metal fluoride into the extraction tube, obtaining the alkali metal dispersion containing the alkali metal fluoride and the alcohol solvent in the extraction tube by refluxing the alcohol solvent and transferring the overflowed liquid phase of the alkali metal dispersion from the extraction tube to the reaction container. The alkali metal fluoride in the form of solid in the extraction tube is disappeared by continuing the reflux operation of the alcohol solvent, thereby being able to transfer all of the alkali metal fluoride to the reaction container. In the present invention, while the reflux operation may be stopped midway through, the reflux operation of the alcohol solvent is preferably conducted continuously until transferring all of the alkali metal fluoride to the reaction container. The mixture in the reaction container obtained by thus operations is usually used as it is for Step (C). Examples of the reaction equipped with the reflux condenser and the extraction tube include a Soxhlet extractor.

Next, Step (C) is illustrated. Step (C) is a step of removing the alcohol solvent from the mixture containing the alkali metal fluoride, which is obtained in the above-mentioned Step (B), to obtain the present dispersion.

Examples of the method of removing the alcohol solvent from the mixture containing the alkali metal fluoride, which is obtained in Step (B), include a solid-liquid separating method such as filtration and decantation, and concentration. Preferably, the obtained mixture is preferably concentrated to remove the alcohol solvent. Alternatively, these methods may be used in combination.

When the alcohol solvent is removed by the solid-liquid separating method, a solid containing no alcohol solvent is obtained, if necessary, by washing the obtained solid with an aprotic organic solvent or drying it, and the obtained solid is mixed with an aprotic organic solvent, thereby being able to obtain the present dispersion.

When the alcohol solvent is removed by concentration, a solvent capable of forming an azeotrope with the alcohol solvent or water may be combined to use from the viewpoint of easier removing of the alcohol solvent. Examples of the solvent capable of forming an azeotrope with the alcohol solvent or water include aromatic hydrocarbon solvents such as benzene, toluene and xylene; and aliphatic hydrocarbon solvents such as hexane and cyclohexane.

The operating pressure during the concentration is usually 0.7 to 200 kPa. The operation temperature is usually 20 to 200° C.

Step (C) and the above-mentioned Step (b3) may be carried out at the same time. Step (C) and Step (b3) are preferably carried out at the same time from the viewpoint of the fluorination ability of the present dispersion obtained.

Examples of the method of conducting Step (C) and Step (b3) at the same time include a method of adjusting the concentrated residue obtained in Step (b1) at a temperature higher than a boiling point of the alcohol solvent at the operation pressure and removing the alcohol solvent by concentrating it with adding the liquid phase separated in Step (b3) thereto.

The present dispersion thus obtained has fluorination ability, and it is practical as a composition for fluorination.

Next, a process for producing a fluorine-containing organic compound by contacting an organic compound having at least one group capable of being substituted nucleophilically with a fluorine atom (hereinafter, simply referred to as the organic compound) with the present dispersion is illustrated.

Examples of the group capable of being substituted nucleophilically with a fluorine atom include a chlorine atom, a bromine atom, an iodine atom, a nitro group, a sulfo group, an optionally substituted alkylsulfonyloxy group, an optionally substituted arylsulfonyloxy group and an optionally substituted acyloxy group. When the organic compound has two or more groups capable of being substituted nucleophilically with a fluorine atom, they may be same or different from each other.

Examples of the optionally substituted alkylsulfonyloxy group include a C1-C4 alkylsulfonyloxy group which may be substituted with a fluorine atom such as a methanesulfonyloxy group, an ethanesulfonyloxy group and a trifluoromethanesulfonyloxy group. Examples of the optionally substituted arylsulfonyloxy group include a C6-C10 arylsulfonyloxy group which may be substituted with a halogen atom or a nitro group such as a p-toluenesulfonyloxy group, a benzenesulfonyloxyl group and a 1-naphthalenesulfonyloxy group. Examples of the optionally substituted acyloxy group include a C2-C10 aliphatic or aromatic acyloxy group which may be substituted with a fluorine atom such as a trifluoroacetoxy group, a pentafluoroethylcarbonyloxy group, a tetrafluorobenzoyloxy group and a benzoyloxy group.

Examples of the organic compound include an aliphatic hydrocarbon compound which has at least one group capable of being substituted nucleophilically with a fluorine atom and which may be substituted with a group not being involved in a fluorination reaction, an aromatic hydrocarbon compound which has at least one group capable of being substituted nucleophilically with a fluorine atom and which may be substituted with a group not being involved in a fluorination reaction, and a heteroaromatic hydrocarbon compound which has at least one group capable of being substituted nucleophilically with a fluorine atom and which may be substituted with a group not being involved in a fluorination reaction. The organic compound is subjected to the fluorination reaction to obtain an organic compound wherein the group capable of being substituted nucleophilically with a fluorine atom is substituted with a fluorine atom.

Examples of the group not being uninvolved in the fluorination reaction include a fluorine atom; a C1-C20 alkoxy group which may be substituted with a fluorine atom such as a methoxy group, an ethoxy group, an n-propoxy group, an isopropoxy group, a butoxy group, an isobutoxy group, a sec-butoxy group, a tert-butoxy group and a trifluoromethoxy group; a C5-C20 aryl group which may be substituted with at least one group selected from the group consisting of a fluorine atom, the above-mentioned alkoxy group and the aryloxy group described below such as a phenyl group, a 1-naphthyl group, a 2-naphthyl group, a 4-methylphenyl group, a 4-methoxyphenyl group, a 3-phenoxyphenyl group, a 2,3,5,6-tetrafluorophenyl group, a 2,3,5,6-tetrafluoro-4-methylphenyl group, a 2,3,5,6-tetrafluoro-4-methoxyphenyl group and a 2,3,5,6-tetrafluoro-4-methoxymethylphenyl group and a 2-pyridyl group; a C6-C20 aryloxy group which may be substituted with at least one group selected from the group consisting of a fluorine atom and the above-mentioned alkoxy group such as a phenoxy group, a 2-methylphenoxy group, a 4-methylphenoxy group, a 4-methoxyphenoxy group and a 3-phenoxyphenoxy group; a C7-C20 aralkyloxy group which may be substituted with at least one group selected from the group consisting of a fluorine atom, the above-mentioned alkoxy group and the above-mentioned aryloxy group such as a benzyloxy group, a 4-methylbenzyloxy group, a 4-methoxybenzyloxy group, a 3-phenoxybenzyloxy group, a 2,3,5,6-tetrafluorobenzyloxy group, a 2,3,5,6-tetrafluoro-4-methylbenzyloxy group, a 2,3,5,6-tetrafluoro-4-methoxybenzyloxy group and a 2,3,5,6-tetrafluoro-4-methoxymethylbenzyloxy group; a C2-C20 acyl group which may be substituted with a fluorine atom such as an acetyl group, an ethylcarbonyl group, a benzoyl group, a 2-methylbenzoyl group, a 4-methylbenzoyl group, a 4-methoxybenzoyl group, a benzylcarbonyl group, a 4-methylbenzylcarbonyl group and a 4-methoxybenzylcarbonyl group; a carboxyl group; an aminosulfonyl group; a cyano group; and a carbamoyl group.

Examples of the unsubstituted aliphatic hydrocarbon compound include a C1-C20 alkane such as methane, ethane, propane, butane, isobutane, pentane, decane, cyclopropane, 2, 2-dimethylcyclopropane, cyclopentane and cyclohexane. Examples of the aliphatic hydrocarbon compound substituted with the group not being uninvolved in the fluorination reaction include fluoromethane, trifluoromethane, methoxymethane, ethoxymethane, methoxyethane, toluene, 4-methoxytoluene, 3-phenoxytoluene, 2,3,5,6-tetrafluorotoluene, 2,3,5,6-tetrafluoro-p-xylene, 2,3,5,6-tetrafluoro-4-methoxytoluene, 2,3,5,6-tetrafluoro-4-methoxymethyltoluene,2-propylnaphthalene, methyl isobutyl ketone, acetophenone, 4-methylacetophenone and phenylacetone.

Examples of the unsubstituted aromatic hydrocarbon compound include a C6-C20 unsubstituted aromatic hydrocarbon compound such as benzene, naphthalene and toluene. Two neighboring groups not being uninvolved in the fluorination reaction may be bonded each other to form a ring together with the carbon atoms to which they are bonded. Examples of the aromatic hydrocarbon compound substituted with the group not being uninvolved in the fluorination reaction include cyanobenzene, terephthalonitrile, isophthalonitrile, orthophthalonitrile, fluorobenzene, 1,4-difluorobenzene, benzenesulfonamide, biphenyl, 2-phenylnaphthalene, diphenyl ether, benzophenone and 1,2-diphenylethanone.

Examples of the unsubstituted heteroaromatic compound include a C5-C20 unsubstituted heteroaromatic compound containing a heteroatom such as nitrogen atom as an atom composing an aromatic ring such as pyridine, quinoline and pyrimidine. Examples of the heteroaromatic compound substituted with the group not being uninvolved in the fluorination reaction include 3-methylpyridine and 4-phenylpyridine.

Specific examples of the organic compound include 1-chlorobutane, 1-bromobutane, 1-iodobutane, 1-chlorocyclobutane, 1-chloropentane, 1-bromopentane, 1-chlorocyclopentane, 1-chloro-4-bromobutane, 1-chlorohexane, 1-bromohexane, 1,6-dibromohexane, 1-chloroheptane, 1-bromoheptane, 2-chloroheptane, 2-bromoheptane, 1-chlorooctane, 1-bromooctane, 2-chlorooctane, 2-bromooctane, benzyl chloride, benzyl bromide, (1-chloroethyl)benzene, (1-bromoethyl)benzene, 4-methoxybenzyl chloride, 4-methylbenzyl bromide, 3,4,5-trifluorobenzyl bromide, n-butyl paratoluenesulfonate, n-butyl methanesulfonate, n-pentyl paratoluenesulfonate, n-pentyl methanesulfonate, n-hexyl paratoluenesulfonate, n-hexyl methanesulfonate, n-heptyl paratoluenesulfonate, n-heptyl methanesulfonate, n-octyl paratoluenesulfonate, n-octyl methanesulfonate, n-butyl trifluoroacetate, n-butyl tetrafluorobenzoate, n-octyl trifluoroacetate, 4-chloronitrobenzene, 4-bromonitrobenzene, 2-chloronitrobenzene, 2-bromonitrobenzene, 2,4-dichloronitrobenzene, 2,6-dichloronitrobenzene, 3,5-dichloronitrobenzene, 4-cyanochlorobenzene, 4-cyanobromobenzene, 1-chloro-2,4-dinitrobenzene, tetrachloroterephthalonitrile, tetrachloroisophthalonitrile, tetrachloroorthophthalonitrile, 1,3-dichloro-4,6-dinitrobenzene, 2-chloroquinoline, 2-chloro-5-nitropyridine, 2-chloro-5-trifluoromethylpyridine and 4,5,6-trichloropyrimidine.

When the organic compound has two or more groups capable of being substituted nucleophilically with a fluorine atom, the fluorine-containing organic compound produced differs depending on the reaction conditions. Only the highest reactive substituent among groups capable of being substituted nucleophilically with a fluorine atom is sometimes substituted with a fluorine atom and all of the groups capable of being substituted nucleophilically with a fluorine atom are sometimes substituted with fluorine atoms.

The fluorine-containing organic compound is obtained by contacting the organic compound with the present dispersion.

When the organic compound having two or more groups capable of being substituted nucleophilically with a fluorine atom is used, groups capable of being substituted nucleophilically with a fluorine atom may be same or different. When the organic compound having two or more different groups capable of being substituted nucleophilically with a fluorine atom is used, only the highest reactive substituent among them is sometimes substituted with a fluorine atom and two or more groups are sometimes substituted with fluorine atoms depending on the reaction conditions.

When the aromatic hydrocarbon compound having two or more groups capable of being substituted nucleophilically with a fluorine atom is used, the group capable of being substituted nucleophilically with a fluorine atom, which has a stronger electron-withdrawing group on para- or ortho-position, is usually substituted preferentially with a fluorine atom. For example, when 4-chloronitrobenzene is used, the chlorine atom at 4-position having stronger electron-withdrawing nitro group on para-position is preferentially substituted with a fluorine atom and 4-fluoronitrobenzene is usually produced selectively. By arbitrarily selecting reaction conditions such as use of a large excess of the present dispersion, 1,4-difluorobenzene wherein the nitro group at 1-position can be also substituted with a fluorine atom in addition to the chlorine atom at 4-position can be also obtained.

When the heteroaromatic compound having two or more groups capable of being substituted nucleophilically with a fluorine atom is used, the group capable of being, substituted nucleophilically with a fluorine atom on 2-, 4- or 6-position against the heteroatom composing the aromatic ring is usually substituted preferentially with a fluorine atom. For example, when 2-chloro-3-nitropyridine is used, the chlorine atom at 2-position against the nitrogen atom composing the pyridine ring is preferentially substituted with a fluorine atom and 2-fluoro-3-nitropyridine is usually produced selectively. By arbitrarily selecting reaction conditions such as use of a large excess of the present dispersion, 2, 3-difluoropyridine wherein the nitro group at 3-position can be also substituted with a fluorine atom in addition to the chlorine atom at 2-position can be also obtained.

The used amount of the present dispersion may be decided arbitrarily depending on the number of the groups desired to substitute with a fluorine atom among groups capable of being substituted nucleophilically with a fluorine atom in the organic compound, and usually, the present dispersion containing 1 mole or more of potassium fluoride per 1 mole of the group desired to substitute with a fluorine atom in the organic compound is used. When the group desired to substitute with a fluorine atom is one, the present dispersion containing 1.5 to 5 moles of potassium fluoride per 1 mole of the organic compound is preferably used from the viewpoint of the reaction efficiency.

The contact of the present dispersion and the organic compound is usually conducted by mixing the both as it is or in the presence of a solvent. The solvent may be a solvent uninvolved in the fluorination reaction, and specific examples thereof include the above-mentioned aprotic polar solvent.

When the contacting temperature is too low, the fluorination reaction hardly proceeds and, when the contacting temperature is too high, side reactions such as degradation of the starting material or product may proceed, and therefore, it is practically 20 to 250° C.

The contact of the present dispersion and the organic compound may be carried out under normal pressure or under pressure. The fluorination reaction of the organic compound proceeds by contacting the present dispersion with the organic compound, and the progress of the fluorination reaction can be checked by a conventional analytical means such as gas chromatography, high performance liquid chromatography, thin layer chromatography, NMR and IR.

After completion of the fluorination reaction, the fluorine-containing organic compound can be isolated, for example, by removing insoluble matters from the obtained reaction mixture by filtration followed by concentrating the obtained filtrate. Alternatively, the fluorine-containing organic compound can also be isolated by adding water and a water-nonmiscible solvent to the reaction mixture to conduct extraction followed by concentrating the obtained organic layer. The fluorine-containing organic compound isolated may be further purified by a conventional purification means such as distillation or column chromatography.

Examples of the water-nonmiscible solvent include aromatic hydrocarbon solvents such as toluene, xylene and chlorobenzene; aliphatic hydrocarbon solvents such as pentane, hexane and heptane; halogenated hydrocarbon solvents such as dichloromethane, dichloroethane and chloroform; ether solvents such as diethyl ether, methyl tert-butyl ether and tetrahydrofuran; and ester solvents such as ethyl acetate.

Examples of the fluorine-containing organic compound thus obtained include 1-fluorobutane, 1-fluorocyclobutane, 1-fluoropentane, 1-fluorocyclopentane, 1,4-difluorobutane, 1-chloro-4-fluorobutane, 1-fluorohexane, 1,6-difluorohexane, 1-fluoroheptane, 2-fluoroheptane, 1-fluorooctane, 2-fluorooctane, benzyl fluoride, (1-fluoroethyl)benzene, 4-methoxybenzylfluoride, 4-methylbenzyl fluoride, 3,4,5-trifluorobenzyl fluoride, 4-fluoronitrobenzene, 2-fluoronitrobenzene, 2,4-difluoronitrobenzene, 2,6-dichlorofluorobenzene, 3,5-difluoronitrobenzene, 4-cyanofluorobenzene, 1-fluoro-2,4-dinitrobenzene, tetrafluoroterephthalonitrile, tetrafluoroisophthalonitrile, tetrafluoroorthophthalonitrile, 1,3-difluoro-4,6-dinitrobenzene, 2-fluoroquinoline, 2-fluoro-5-nitropyridine, 2-fluoro-5-trifluoromethylpyridine, 4,6-difluoro-5-chloropyrimidine and 4,5,6-trifluoropyrimidine.

While the method for producing the fluorine-containing organic compound is specifically illustrated below by drawing the case where tetrachloroterephthaloyl dichloride is used as the organic compound, the present invention is not limited to this. Tetrafluoroterephthaloyl difluoride can be produced by using tetrachloroterephthaloyl dichloride as the organic compound. Tetrafluoroterephthaloyl difluoride is a useful compound as a law material of pharmaceuticals or agrichemicals (e.g. CN 1458137 A and JP 2606892 B).

Tetrachloroterephthaloyl dichloride can be produced, for example, according to known methods described in JP 2-11571 B or the like.

The used amount of the present dispersion may usually be an amount of the dispersion containing 6 moles or more of the alkali metal fluoride per 1 mole of tetrachloroterephthaloyl dichloride. While there is no specific upper limit, it is preferably 10 moles or less per 1 mole of tetrachloroterephthaloyl dichloride from the economic viewpoint.

The present dispersion is preferably contacted with tetrachloroterephthaloyl dichloride at 120 to 200° C.

After completion of the reaction, tetrafluoroterephthaloyl difluoride can be isolated, for example, by concentrating the reaction mixture. Isolated tetrafluoroterephthaloyl difluoride may be further purified by a conventional purification means such as rectification.

Alternatively, the corresponding tetrafluoroterephthalic acid diester can be also produced by reacting obtained tetrafluoroterephthaloyl difluoride with an aliphatic alcohol.

Tetrafluoroterephthaloyl difluoride may be reacted with the aliphatic alcohol as it is without isolating from the above-mentioned reaction mixture.

Examples of the aliphatic alcohol include a C1-C6 aliphatic alcohol represented by the following formula (1)

$$R'OH \quad (1)$$

wherein R' represents a C1-C6 alkyl group, such as methanol, ethanol, n-propanol, isopropanol, n-butanol, tert-butanol and cyclohexanol.

When the alcohol represented by the formula (1) is used, tetrafluoroterephthalic acid diester represented by the formula (2)

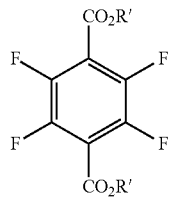

(2)

wherein R' represents the same meanings as defined above, is obtained.

The used amount of the aliphatic alcohol is not limited. While the excess amount thereof may be used also to serve as the solvent, the practical amount thereof is 2 to 50 moles per 1 mole of tetrafluoroterephthaloyl difluoride.

When the reaction mixture containing tetrafluoroterephthaloyl difluoride is used as it is, the reaction can be carried out by mixing the reaction mixture with the aliphatic alcohol as they are. When tetrafluoroterephthaloyl difluoride is isolated from the reaction mixture to use, tetrafluoroterephthaloyl difluoride is preferably reacted with the aliphatic alcohol in the presence of an organic solvent. Examples of the organic solvent include aromatic hydrocarbon solvents such as toluene, xylene and chlorobenzene;

aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; and ester solvents such as ethyl acetate. The used amount of the organic solvent is not limited.

The reaction of tetrafluoroterephthaloyl difluoride with the aliphatic alcohol compound is usually conducted by mixing the both and the mixing order thereof is not particularly limited.

The reaction temperature is usually 0 to 100° C. While the reaction is usually carried out under normal pressure, the reaction may be conducted under pressure.

The progress of the reaction can be checked by a conventional analytical means such as gas chromatography and high performance liquid chromatography.

After completion of the reaction, the tetrafluoroterephthalic acid diester can be isolated by concentrating the reaction mixture, if necessary, after removing insoluble matters by filtration, followed by mixing the obtained concentrated residue with water to separate the solid of the tetra fluoroterephthalic acid diester precipitated by filtration. Alternatively, the tetrafluoroterephthalic acid diester can also be isolated by mixing the reaction mixture, water and as necessary, a water-nonmiscible solvent to conduct separation treatment followed by concentrating the obtained organic layer. Examples of the water-nonmiscible solvent include aromatic hydrocarbon solvents such as toluene, xylene and chlorobenzene; aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; and ester solvents such as ethyl acetate. The used amount thereof is not particularly limited.

The tetrafluoroterephthalic acid diester isolated may be further purified by a conventional purification means such as crystallization and column chromatography.

Examples of the tetrafluoroterephthalic acid diester thus obtained include dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate and di(tert-butyl) 2,3,5,6-tetrafluoroterephthalate.

EXAMPLES

The present invention is illustrated in more detail by Examples below. The present invention is not limited to these Examples.

Example 1

Into a 200 mL flask equipped with a reflux condenser and a Soxhlet extractor, 30 g of methanol and 100 g of toluene were added. To the Soxhlet extractor, 20 g of potassium fluoride (purchased from NAKALAI TESQUE, INC.; commodity code 28611-95) was charged. The mixture in the flask was heated at 100° C. under a normal pressure and methanol was refluxed for 18 hours at the same temperature. As the result, potassium fluoride in the Soxhlet extractor was completely disappeared and a potassium fluoride dispersion was obtained in the flask. The potassium fluoride dispersion was concentrated at 90 to 100° C. under a normal pressure to remove 100 g of methanol/toluene mixed liquid. The obtained mixture was filtrated, and the obtained fine powder was dried to obtain 19.7 g of potassium fluoride. It was visually confirmed that the particle diameter of the obtained potassium fluoride was smaller than that of potassium fluoride charged into the Soxhlet extractor.

To a 50 mL flask equipped with a reflux condenser and a water separation tube, 960 mg of the obtained potassium fluoride, 3 g of sulfolane and 3 g of toluene were charged, and the obtained mixture was refluxed at 130° C. for 30 minutes under a normal pressure. During that time, water was separated from a reflux liquid in the water separation tube and removed out the system. Further, it was heated at 140° C. to distil toluene away to obtain a potassium fluoride dispersion essentially consisting of potassium fluoride and sulfolane.

The potassium fluoride dispersion was cooled down to 100° C. and was mixed with 680 mg of tetrachloroterephthaloyl dichloride. The obtained mixture was stirred for 4 hours at 150° C. to effect reaction.

The obtained reaction mixture was cooled down to room temperature and then, 5 g of methanol was added to stir for 1 hour. Further, 10 g of ethyl acetate was added thereto to obtain a mixture containing dimethyl 2,3,5,6-tetrafluoroterephthalate. The obtained mixture was analyzed with gas chromatography internal standard method. Yield of dimethyl 2,3,5,6-tetrafluoroterephthalate: 70% Yield of dimethyl 2,3,5-trifluoro-6-chloroterephthalate: 16% Yield of dimethyl difluoro-dichloroterephthalate (sum of three kinds of isomers): 11%

Example 2

Into a 1 L flask equipped with a reflux condenser, 500 g of sulfolane was added and was adjusted at an inner temperature of 140° C. Alternatively, 150 g of potassium fluoride (purchased from NAKALAI TESQUE, INC.; commodity code 28611-95) and 500 g of methanol were charged into a 2 L Erlenmeyer flask to stir at room temperature to obtain a mixture of a liquid phase containing potassium fluoride and a solid phase consisting of potassium fluoride. The liquid phase of the mixture was separated by decantation and the separated liquid phase was added dropwise to sulfolane adjusted at an inner temperature of 140° C. together with removing the distilled methanol out the system to obtain a mixture containing potassium fluoride and sulfolane. The distilled methanol was mixed with the residue after separating the liquid phase by decantation and a liquid phase was separated from the obtained mixture. The mixture containing potassium fluoride and sulfolane, which was obtained above, was adjusted at an inner temperature of 140° C., and methanol was distilled away with adding dropwise the separated liquid phase thereto to obtain a concentrated liquid containing potassium fluoride.

The above-mentioned operation was repeated until disappearing the solid phase of potassium fluoride.

After methanol was hardly distilled out from the concentrated liquid containing potassium fluoride at all, the concentration was further continued under the condition of 160° C./2.7 kPa to obtain a potassium fluoride dispersion essentially consisting of potassium fluoride and sulfolane. It was visually confirmed that the particle diameter of potassium fluoride in the obtained dispersion was smaller than that of potassium fluoride charged into the Erlenmeyer flask.

The obtained potassium fluoride dispersion was cooled down to 100° C. and was mixed with 110 g of tetrachloroterephthaloyl dichloride. The obtained mixture was stirred for 10 hours at 145° C. to effect reaction. The obtained reaction mixture was cooled down to 100° C. and 300 g of toluene was added thereto and then cooled down to room temperature. To the obtained mixture, 75 g of methanol was added dropwise to stir for 12 hours at room temperature while removing hydrogen fluoride gas generated as by-product out the flask using nitrogen gas. The precipitated solid was separated by filtration and the obtained solid was washed with 30 g of toluene. The filtrate and wash liquid were mixed and 500 g of water was added thereto, and then 4 g of potassium carbonate was added thereto to adjust pH of an aqueous layer to 8. The obtained mixture was separated into an organic layer and an aqueous layer. The organic layer was concentrated with an evaporator (operating pressure: 10 to 100 kPa, water bath temperature: 30 to 50° C.) to obtain the oily residue. The residue was mixed with 400 g of water, thereby precipitating crystals. The mixture was concentrated with an evaporator (operation pressure: 10 to 100 kPa, water bath temperature: 30 to 50° C.) to remove toluene contained therein as an azeotrope of toluene and water. The concentrated liquid was cooled down to room temperature and the crystals were separated by filtration, and dried to obtain 82.2 g of pale yellow crystals. The crystals were analyzed with gas chromatography area percentage method. The purity of dimethyl 2,3,5,6-tetrafluoroterephthalate was 89%. Isolated yield: 85%.

Example 3

To a 50 mL flask equipped with a reflux condenser and a water separation tube, 700 mg of potassium fluoride prepared in Example 1, 4 g of dimethylsulfoxide and 5 g of toluene were charged, and the obtained mixture was refluxed at 130° C. for 30 minutes under a normal pressure. During that time, water was separated from a reflux liquid in the water separation tube and removed out the system. Further, toluene was distilled away at 140° C. to obtain a potassium fluoride dispersion essentially consisting of potassium fluoride and dimethylsulfoxide.

The obtained potassium fluoride dispersion was cooled down to 100° C. and was mixed with 1.2 g of 4-chloronitrobenzene. The obtained mixture was stirred for 5 hours at 185° C. to effect reaction. The reaction mixture was cooled down to 100° C., and 100 g of toluene was added thereto to cool down to room temperature. The precipitated solid was separated by filtration and the obtained solid was washed with 10 g of toluene. The filtrate and the wash liquid were mixed to obtain a solution containing 4-fluoronitrobenzene. The obtained solution was analyzed with gas chromatography internal standard method.
Yield of 4-fluoronitrobenzene: 85%
Recovery ratio of 4-chloronitrobenzene: 15%

Comparative Example 1

Into a 50 mL flask equipped with a reflux condenser, 960 mg of potassium fluoride (purchased from NAKALAI TESQUE, INC.; commodity code 28611-95) and 2 g of methanol were charged to reflux for 30 minutes, and however, potassium fluoride was not dissolved completely, and a mixture of a liquid phase containing potassium fluoride and a solid phase consisting of potassium fluoride was obtained. To the obtained mixture, 3 g of sulfolane and 3 g of toluene were added to concentrate at 130° C. at a normal pressure to remove methanol/toluene mixed liquid. After methanol was hardly distilled at all, the concentration was further continued at 140° C. to remove toluene, thereby obtaining a potassium fluoride dispersion.

The obtained potassium fluoride dispersion was cooled down to 100° C. and mixed with 680 mg of tetrachloroterephthaloyl dichloride. The obtained mixture was stirred for 4 hours at 150° C. to effect reaction. The reaction mixture was cooled down to room temperature and then, 5 g of methanol was added thereto to stir at room temperature for 1 hour. To the obtained mixture, 10 g of ethyl acetate was added followed by being analyzed with gas chromatography internal standard method.
Yield of dimethyl 2,3,5,6-tetrafluoroterephthalate: 0%
Yield of dimethyl 2,3,5-trifluoro-6-chloroterephthalate: 0%
Yield of dimethyl difluoro-dichloroterephthalate (sum of three kinds of the isomers): 0%
Yield of dimethyl 2-fluoro-3,5,6-trichloroterephthalate: 1%
Yield of dimethyl 2,3,5,6-tetrachloroterephthalate: 98%

Example 4

Into a 100 mL flask equipped with a reflux condenser, 15 g of sulfolane was added and was adjusted at an inner temperature of 120° C. Into a 100 mL Erlenmeyer flask, 4.3 g of cesium fluoride (purchased from KANTO CHEMICAL CO., INC.; commodity code 07186-33) and 10 g of methanol were charged to stir at room temperature to obtain a mixture of a liquid phase containing cesium fluoride and a solid phase consisting of cesium fluoride. The liquid phase of the mixture was separated by decantation. The separated liquid phase was added dropwise to sulfolane adjusted at an inner temperature of 120° C. together with removing the distilled methanol out the system to obtain a mixture containing cesium fluoride and sulfolane. The distilled methanol was mixed with the residue after separating the liquid phase by decantation and a liquid phase was separated from the obtained mixture. The mixture containing cesium fluoride and sulfolane, which was obtained above, was adjusted at an inner temperature of 120° C., and methanol was distilled away with adding dropwise the separated liquid phase thereto to obtain a concentrated liquid containing potassium fluoride.

The above-mentioned operation was repeated until disappearing the solid phase of cesium fluoride.

After methanol was hardly distilled out from the concentrated liquid containing cesium fluoride at all, the concentration was further continued under the condition of 140° C./2.7 kPa to obtain a cesium fluoride dispersion essentially consisting of cesium fluoride and sulfolane. It was visually confirmed that the particle diameter of cesium fluoride in the obtained dispersion was smaller than that of cesium fluoride charged into the 100 mL Erlenmeyer flask.

The obtained cesium fluoride dispersion was cooled down to 100° C. and was mixed with 3.0 g of 4-chloronitrobenzene. The obtained mixture was stirred for 2 hours at 140° C. to effect reaction. The reaction mixture was cooled down to room temperature and diluted with 20 g of dichloromethane. The obtained mixture was analyzed with gas chromatography internal standard method.
Yield of 4-fluoronitrobenzene: 64%
Recovery ratio of 4-chloronitrobenzene: 35%

Example 5

Into a 100 mL flask equipped with a reflux condenser, 15 g of sulfolane was added and was adjusted at an inner temperature of 140° C. Into a 100 mL Erlenmeyer flask, 4.3 g of cesium fluoride (purchased from KANTO CHEMICAL CO., INC.; commodity code 07186-33) and 10 g of ethanol were charged to stir at room temperature to obtain a mixture of a liquid phase containing cesium fluoride and a solid phase consisting of cesium fluoride. The liquid phase of the mixture was separated by decantation. The separated liquid phase was added dropwise to sulfolane adjusted at an inner temperature of 140° C. in the 100 mL flask together with removing the distilled ethanol out the system to obtain a mixture containing cesium fluoride and sulfolane. The distilled ethanol was mixed with the residue after separating the liquid phase by decantation and a liquid phase was separated from the obtained mixture. The mixture containing cesium fluoride and sulfolane, which was obtained above, was adjusted at an inner temperature of 140° C., and ethanol was distilled away with adding dropwise the separated liquid phase thereto to obtain a concentrated liquid containing cesium fluoride.

The above-mentioned operation was repeated until disappearing the solid phase of cesium fluoride.

After ethanol was hardly distilled out from the concentrated liquid containing cesium fluoride at all, the concentration was further continued under the condition of 160° C./2.7 kPa to obtain a cesium fluoride dispersion essentially consisting of cesium fluoride and sulfolane. It was visually confirmed that the particle diameter of cesium fluoride in the obtained dispersion was smaller than that of cesium fluoride charged into the 100 mL Erlenmeyer flask.

The obtained cesium fluoride dispersion was cooled down to 100° C. and was mixed with 3.0 g of 4-chloronitrobenzene. The obtained mixture was stirred for 2 hours at 140° C. to effect reaction. The reaction mixture was cooled down to room temperature and diluted with 20 g of dichloromethane. The obtained mixture was analyzed with gas chromatography internal standard method.
Yield of 4-fluoronitrobenzene: 57%
Recovery ratio of 4-chloronitrobenzene: 42%

Comparative Example 5

Into a 50 mL flask equipped with a reflux condenser, 7.5 g of sulfolane, 2.2 g of cesium fluoride (purchased from KANTO CHEMICAL CO., INC.; commodity code 07186-33) and 1.5 g of 4-chloronitrobenzene were charged. The obtained mixture was stirred for 2 hours at 140° C. to effect reaction. The reaction mixture was cooled down to room temperature and diluted with 20 g of dichloromethane. The obtained mixture was analyzed with gas chromatography internal standard method.
Yield of 4-fluoronitrobenzene: 25%
Recovery ratio of 4-chloronitrobenzene: 74%

Industrial Applicability

The potassium fluoride dispersion of the present invention has high fluorination ability and fluorine-containing organic compounds, which are important as various chemicals such as pharmaceuticals, agrichemicals and electronic materials and its synthetic intermediates, can be produced efficiently without using an expensive phase transfer catalyst, and therefore, it is industrially advantageous.

The invention claimed is:
1. A process for producing an alkali metal fluoride dispersion consisting essentially of an alkali metal fluoride and an aprotic organic solvent obtained by conducting the following (A), subsequently conducting the following (B) at least once, and then conducting the following (C):
   (A): separating a liquid phase from a residue of an alkali metal fluoride dispersion comprising at least one alcohol solvent selected from the group consisting of methanol, ethanol and isopropanol and an alkali metal fluoride, and mixing the separated liquid phase with an aprotic organic solvent having a boiling point of 85° C. or higher at normal pressure to obtain a mixture containing the alkali metal fluoride,
   wherein the liquid phase comprises the alkali metal fluoride and the alcohol solvent, and
   wherein the amount of the alcohol solvent used in (A) is less than 5 parts by weight per 1 part by weight of the alkali metal fluoride;
   (B): obtaining a mixture containing the alkali metal fluoride comprising by applying at least the following (31) to (b3);
      (b1): concentrating the mixture containing the alkali metal fluoride, which is obtained in (A) or (b3), to obtain a concentrated fraction and a concentrated residue;
      (b2): mixing a residue of the alkali metal fluoride dispersion obtained by the separating the liquid phase in (A) or a residue of the mixture obtained by separating a liquid phase in (b3) with the concentrated fraction obtained in (b1), to obtain a mixture containing an alkali metal fluoride; and
      (b3): separating a liquid phase from the mixture containing an alkali metal fluoride, which is obtained in (b2), and mixing the separated liquid phase with the con- centrated residue obtained in (b1), to obtain a mixture containing an alkali metal fluoride; and (C): removing the alcohol solvent from the mixture containing the alkali metal fluoride, which is obtained in (B), to obtain the alkali metal fluoride dispersion essentially consisting of the alkali metal fluoride and the aprotic organic solvent.

2. The process according to claim 1, wherein the concentrated fraction obtained in (b1) is a fraction essentially consisting of the alcohol solvent.

3. The process according to claim 1, wherein (A) to (B) is continuously conducted.

4. The process according to claim 1, wherein the alkali metal fluoride is potassium fluoride or cesium fluoride.

5. The process according to claim 1, wherein the alcohol solvent is methanol or ethanol.

6. The process according to claim 1, wherein the alkali metal fluoride is potassium fluoride and the alcohol solvent is methanol.

7. The process according to claim 1, wherein the aprotic organic solvent is an aprotic polar solvent.

8. The process according to claim 7, wherein the aprotic polar solvent is a sulfone solvent or a sulfoxide solvent.

* * * * *